(12) United States Patent
Varlet et al.

(10) Patent No.: US 11,284,848 B2
(45) Date of Patent: Mar. 29, 2022

(54) X-RAY CT IMAGING METHOD, INTERFACE SYSTEM AND APPARATUS

(71) Applicant: TROPHY, Croissy-Beaubourg (FR)

(72) Inventors: Stephane Varlet, Chenehutte (FR); Stephane Alric, Paris (FR); Aude Lagardere, Paris (FR)

(*) Notice: Subject to any disclaimer, the term of this patent is extended or adjusted under 35 U.S.C. 154(b) by 0 days.

(21) Appl. No.: 16/627,000

(22) PCT Filed: Jun. 30, 2017

(86) PCT No.: PCT/IB2017/001010
§ 371 (c)(1),
(2) Date: Dec. 27, 2019

(87) PCT Pub. No.: WO2019/002904
PCT Pub. Date: Jan. 3, 2019

(65) Prior Publication Data
US 2020/0138390 A1    May 7, 2020

(51) Int. Cl.
*A61B 6/00* (2006.01)
*A61B 6/03* (2006.01)
*G06T 7/00* (2017.01)

(52) U.S. Cl.
CPC .............. *A61B 6/463* (2013.01); *A61B 6/465* (2013.01); *A61B 6/469* (2013.01); *G06T 7/0012* (2013.01);
(Continued)

(58) Field of Classification Search
CPC ......... A61B 6/463; A61B 6/465; A61B 6/469; A61B 6/032; A61B 6/5223; A61B 6/5258;
(Continued)

(56) References Cited

U.S. PATENT DOCUMENTS

| | | | |
|---|---|---|---|
| 2013/0070991 A1* | 3/2013 | Yang | G06K 9/00389 382/131 |
| 2016/0078647 A1* | 3/2016 | Schildkraut | G06T 11/005 382/131 |

(Continued)

OTHER PUBLICATIONS

Nam et al., A metal artifact reduction algorithm in CT using multiple prior images by recursive active contour segmentation, Jun. 12, 2017, PLOS one, pp. 1-21 (Year: 2017).*

(Continued)

*Primary Examiner* — Christine S. Kim (57) ABSTRACT

Certain exemplary method and/or apparatus embodiments herein can include—acquiring a set of data relative to a patient's maxillofacial region through an x-ray CT imaging apparatus, —reconstructing two or more types of maxillofacial data volumes from the same acquired set of data, —displaying at least one slice of the patient's maxillofacial region with a first type of data volume among the volumes (e.g., FDK volume and MAR volume), —selecting a region of interest (ROI) in the displayed at least one slice, a first portion of said first type of data volume being displayed within the ROI, —displaying within the selected ROI a second portion of a second type of data volume, the at least one slice of the patient's maxillofacial region being displayed with the first type of data volume while the ROI is displayed with the second portion of the second type of data volume.

15 Claims, 6 Drawing Sheets

(52) U.S. Cl.
CPC ..... *A61B 6/032* (2013.01); *G06T 2207/10081* (2013.01)

(58) Field of Classification Search
CPC ... A61B 6/5202; A61B 6/5229; A61B 6/4085; A61B 6/4435; G06T 7/0012; G06T 2207/10081
See application file for complete search history.

(56) References Cited

U.S. PATENT DOCUMENTS

2019/0139272 A1* 5/2019 Pan .................... G06T 11/006
2020/0151921 A1* 5/2020 Schildkraut .......... G06K 9/6268

OTHER PUBLICATIONS

Wu, Meng, Metal artifact correction for x-ray computed tomography using kV and selective MV imaging, Dec. 2014, Med Phys, vol. 41, pp. 1-15 (Year: 2014).*

* cited by examiner

X-RAY CT IMAGING METHOD, INTERFACE SYSTEM AND APPARATUS

TECHNICAL FIELD

The disclosure relates generally to the field of dental x-ray imaging and in particular to the field of x-ray CT (Computed Tomography) imaging. More specifically, the disclosure relates to a method for obtaining a radiographic image of a patient's mouth through x-ray data acquisition, an x-ray CT imaging interface system and an x-ray CT imaging apparatus.

BACKGROUND

Conventional methods for obtaining a radiographic image of a patient's maxillofacial region through x-ray CT imaging generally comprise:

- acquiring a set of data (2D projections) relative to a patient's maxillofacial region through an x-ray CT imaging apparatus,
- reconstructing a radiographic 3D image of the patient's maxillofacial region after data processing has been performed on the acquired set of data,
- displaying the reconstructed dental image for subsequent interpretation by a practitioner.

The presence of metal in a patient's maxillofacial region such as metallic implants may seriously affect the visual quality and interpretability of dental images.

In this respect, a metal artifact reduction (MAR) algorithm may be used to effectively reduce metal streaks artifacts and enhance the contrast-to-noise ratio in most cases.

However, the MAR algorithm can also generate information that is close to that generated by metal. Depending on the metal repartition in the patient's mouth the contrast-to-noise ratio may then be reduced. In this respect, a FDK algorithm may be used to avoid the drawbacks associated with the MAR algorithm.

Given the above, the practitioner then needs two types of images for comparison purpose in order to avoid a misdiagnosis: a first image reconstructed with a first FDK data volume and a second image reconstructed with a second MAR data volume. While such methods may have achieved certain degrees of success in their particular applications, there is a need to simplify the comparison between the two types of images.

SUMMARY

An object of the present disclosure is to simplify the task of a practitioner.

Another object of the present disclosure is to simplify the comparison between a first image reconstructed with a first FDK data volume and a second image reconstructed with a second MAR data volume.

A further object of the present disclosure is to avoid misdiagnosis for a practitioner.

These objects are given only by way of illustrative example, and such objects may be exemplary of one or more embodiments of the invention. Other desirable objectives and advantages inherently achieved by the may occur or become apparent to those skilled in the art. The invention is defined by the appended claims.

According to one aspect of the disclosure, there is provided certain exemplary method and/or apparatus embodiments for obtaining a radiographic image of a patient's maxillofacial region through x-ray CT imaging, more particularly, through CBCT (Cone Beam Computed Tomography) imaging, such exemplary method and/or apparatus embodiments comprising:

- acquiring a set of data relative to a patient's maxillofacial region through an x-ray CT imaging apparatus, more particularly, a CBCT imaging apparatus,
- reconstructing two types of data volumes from the same acquired set of data i.e. a FDK volume and a MAR (Metal Artefact Reduction) volume that both correspond to the same maxillofacial region,
- displaying at least one slice of the patient's maxillofacial region with a first type of data volume among the FDK volume and the MAR volume,
- selecting a region of interest (ROI) in the displayed at least one slice, the ROI corresponding to a first portion of said first type of data volume,
- displaying within the selected ROI a second portion of a second type of data volume, the at least one slice of the patient's maxillofacial region being displayed with the first type of data volume while the ROI is displayed with the second portion of the second type of data volume.

Additional possible exemplary method and/or apparatus embodiments features or aspects:

- prior to displaying within the selected ROI the second portion of the second type of data volume, the method comprises determining the second portion of the second type of data volume among the FDK volume and the MAR volume corresponding to the selected ROI;
- the at least one slice of the patient's maxillofacial region comprises a slice in a coronal view, a slice in a facial view and a slice in a sagittal view;
- the ROI is selected among any of the three slices.
- the method further comprises displaying another parallel slice within the same view with the same displayed ROI instead of the previous at least one slice;
- displaying within the selected ROI the second portion of the second type of data volume comprises replacing the first portion of the first type of data volume with the second portion of the second type of volume;
- displaying within the selected ROI the second portion of the second type of data volume comprises superimposing the second portion of the second type of data volume on the first portion of the first type of data volume;
- the method further comprises displaying on the displayed at least one slice an indicator representative of the type of data volume that is used for displaying the at least one slice;
- the method further comprises displaying an indicator representative of the type of data volume that is displayed within the ROI;
- selecting the ROI in the displayed at least one slice comprises beforehand activating a comparison tool FDK volume/MAR volume and moving a pointing device on the displayed at least one slice to a zone of the slice corresponding to the selected ROI;
- the method stops displaying within the selected ROI the second portion of a second type of data volume among the FDK volume and the MAR volume so that the whole at least one slice of the patient's mouth including the ROI is displayed with the first type of data volume;
- the ROI is bounded by an apparent outline;
- the bounding outline can take any preset or freehand shape;

the bounding outline can be visually continuous or intermittent (e.g., dashed);

the bounding outline has a size that can be adjusted.

According to another exemplary aspect of the disclosure, there is provided an x-ray CT imaging interface system, more particularly, exemplary method and/or apparatus CBCT imaging interface embodiments comprising:

a display assembly for displaying a radiographic image of the patient's maxillofacial region, a user interface assembly that can be operated by a user for selecting a zone on the displayed image in cooperation with the display assembly, a processor configured to:

display on the display assembly at least one slice of the patient's maxillofacial region with a first type of data volume among a FDK volume and a MAR (Metal Artefact Reduction) volume that respectively correspond to reconstructed data volumes of the same maxillofacial region through x-ray CT imaging, more particularly, through CBCT imaging, identify, on the displayed at least one slice, a region of interest (ROI) that has been selected by a user through the user interface assembly and that contains a first portion of the first type of data volume, display, within the selected ROI, a second portion of a second type of data volume so that the at least one slice of the patient's maxillofacial region is displayed with the first type of data volume while the ROI is displayed with the second portion of the second type of data volume.

According to still another exemplary aspect of the disclosure, there is provided an x-ray CT imaging apparatus, more particularly, a CBCT imaging apparatus, comprising the above x-ray CT imaging interface system, more particularly, the above CBCT imaging interface system, wherein the x-ray CT imaging apparatus, more particularly, the CBCT imaging apparatus, is configured to:

acquire a set of data relative to the patient's maxillofacial region through an x-ray CT imaging acquisition process, more particularly, through a CBCT imaging acquisition process, reconstruct the two types (or three or more of data volumes from the same acquired set of data e.g., the FDK volume, the MAR (Metal Artefact Reduction) volume, and a third or more volume reconstruction that all correspond to the same maxillofacial region.

According to yet another exemplary aspect of the disclosure, there is provided a computer storage medium having instructions stored therein for causing a computer or control assembly to perform exemplary method and/or apparatus embodiments as briefly described above.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

DETAILED DESCRIPTION OF THE EMBODIMENTS

The following is a description of exemplary method and/or apparatus embodiments of the application, reference being made to the drawings in which the same reference numerals identify the same elements of structure in each of the several figures.

Figure 1:
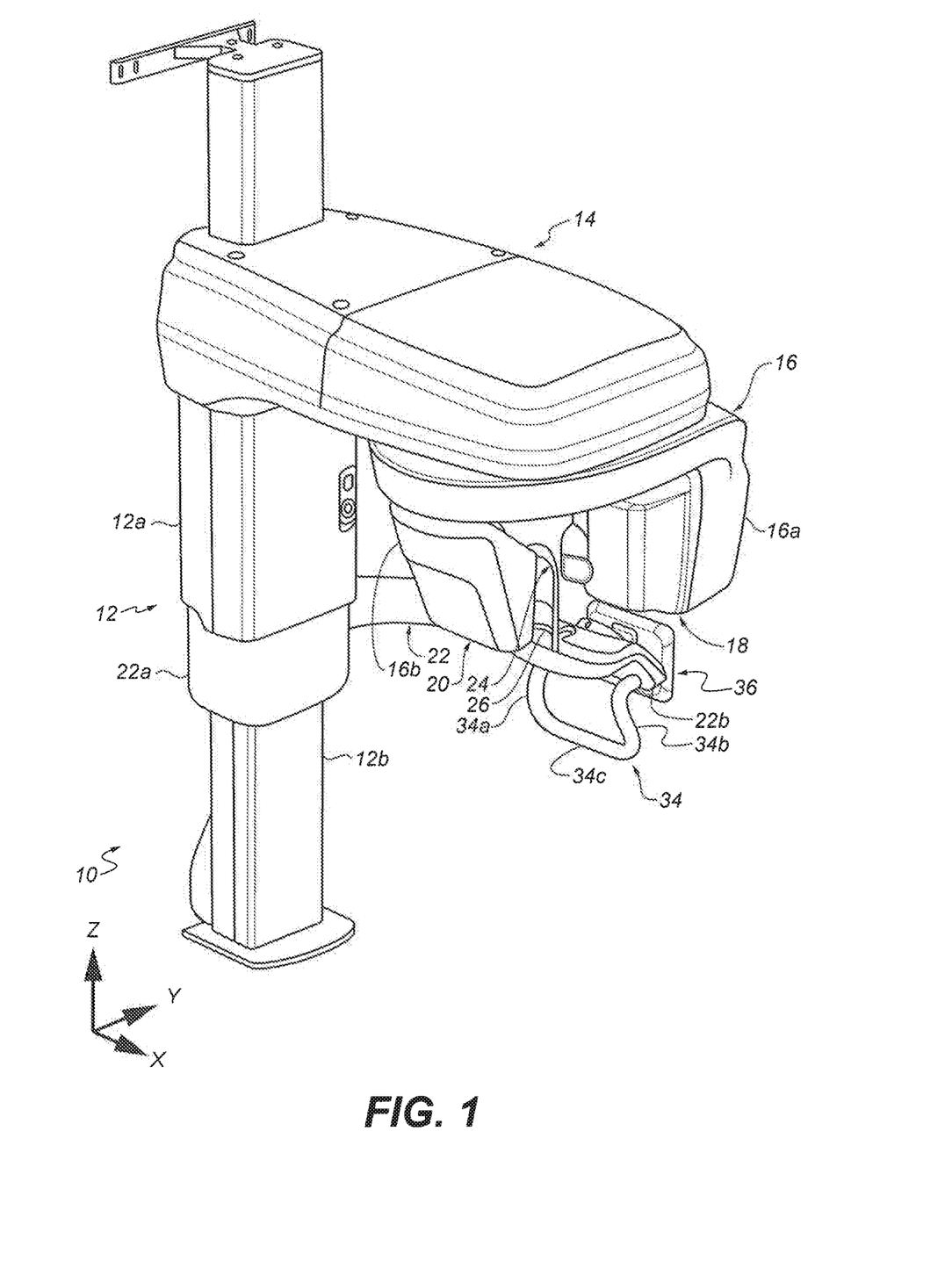
FIG. 1 shows an overall schematic perspective view of an extra-oral imaging apparatus according to an embodiment of the invention.

FIG. 1 illustrates an embodiment of an extra-oral imaging apparatus 10. Apparatus 10 comprises a support structure that includes a support frame 12 which may be a support column.

The support structure also includes a horizontal mount 14 that may be supported or held by the vertical column 12. Horizontal mount 14 extends away from vertical column 12 and may be substantially perpendicular thereto. Horizontal mount 14 can move vertically relative to the vertical column 12.

More particularly, horizontal mount 14 is fixedly mounted on a vertical part 12a that is slidably mounted over a fixed vertical part 12b. For example, an actuator, e.g. of the electric type, located behind the vertical column (not represented in the drawing) can be commanded to drive the horizontal mount 14 into a vertical movement in a controlled manner.

Horizontal mount 14 can support a gantry 16. Gantry 16 is movable relative to the support structure, and more particularly to horizontal mount 14. Gantry 16 may more particularly be rotatable relative to horizontal mount 14. Gantry 16 may be rotatable about a vertical axis of rotation which may be stationary during the operation of the imaging process or may follow one among several predetermined trajectories in accordance with the selected imaging process. A driving known mechanism (not represented in the drawing) for driving the gantry 16 into a given movement is integrated inside horizontal mount 14. By way of example, such driving mechanism includes motors for imparting a first movement in a X, Y plane (e.g., X plane, Y plane, X and Y plane), e.g. two step by step motors, and a motor for imparting a rotational movement (e.g., about the vertical axis Z), e.g. a brushless motor.

Gantry 16 supports both an x-ray source 18 and at least one x-ray sensor 20 that is arranged in correspondence with the x-ray source. X-ray source 18 and the at least one x-ray sensor 20 may be arranged facing each other. Gantry 16 may include two opposite downwardly extending arms: a first arm 16a supports x-ray source 18 that is attached thereto and a second opposite arm 16b supports the at least one x-ray sensor 20 that is attached thereto.

When activated x-ray source 18 emits an x-ray beam, which here can radiate an imaging area of the patient's maxillofacial region, before impinging the at least one x-ray sensor 20.

In the present exemplary embodiment the apparatus 10 is used in an x-ray CT operating mode and here, more particularly, in a CBCT operating mode. The apparatus 10 is considered as an x-ray CT imaging apparatus and here, more particularly, as a CBCT imaging apparatus, to perform volumetric or computerized tomography and obtain 3D images.

However, the apparatus 10 may also function according to one or several other operating modes or imaging processes, such as projection, panoramic, cephalometric, etc.

In this respect, another sensor or other sensors may be used and the x-ray may be collimated accordingly to irradiate a region of the patient's head (or the whole patient's head) with a specific shape depending on the selected operating mode and choice of the practitioner.

In the present exemplary embodiment the x-ray beam is cone-shaped or substantially cone-shaped (ex: a frusto-conical shape).

The at least one x-ray sensor 20 includes a sensor that is adapted to a CBCT scan, e.g. a volumetric or computerized sensor (e.g. rectangular, square-shaped), or several sensors of the previous type.

The support structure may also include a patient positioning accessory support member 22 which here is an arm. Arm 22 is connected to the support frame, and more particularly to the vertical column 12. The patient positioning arm 22 is movable relative to the support frame. More particularly, arm 22 can slide along the vertical column 12 so as to move up or down upon command through appropriate actuator(s) e.g., of the electric type. The patient positioning arm 22 extends from an arm support 22a that is movably (e.g., slidably) mounted relative to the fixed vertical part 12b. The patient positioning arm 22 extends along the apparatus in a direction that is substantially in correspondence with the direction of extension of horizontal mount 14. Here exemplary patient positioning arm 22 is arranged sideways relative to the apparatus in a substantial parallel relationship with horizontal mount 14.

Patient positioning arm 22 serves to position the patient in the apparatus at a given location.

Patient positioning arm 22 may include one of several patient positioning accessories generally located at a free end 22b of the arm or proximate thereto. These accessories may also or alternatively be considered as holding systems. These patient positioning accessories allow to position the anatomical structures of the patient's head according to different orientations and to partly restrain or immobilize the patient's head during the examination so as to reduce any possible movement.

There exist one or several types of patient positioning accessories for each type of specific examination to be carried out by the apparatus according to different operating modes. The arm 22 is configured to accommodate each of these patient positioning accessories of different types, generally one at a time.

As illustrated in FIG. 1, one of these patient positioning accessories, noted 24, includes two temporal holding members that extend upwardly from the arm 22 to which they are removably attached. Only one temporal holding member is represented, the other one being hidden by the arm 16b.

The patient positioning accessory 24 also includes a chin rest 26 that extends upwardly from the arm 22 to which it is removably attached. The chin rest 26 is located between the two temporal holding members to position a patient's head for a panoramic examination.

Other possible types of patient positioning accessories may be envisaged: a nasal support for conducting a temporal mandible joint examination with open and closed mouth, a bitten support for 3D examination (bit type), a frontal support 32 for 3D examination (frontal type), etc.

As illustrated in FIG. 1, a handle assembly 34 may be positioned at the free end 22b of the arm, underneath the arm and in a parallel relationship with the arm. This handle assembly 34 includes two vertical separate handle portions 34a, 34b which can be grasped by the patient when undergoing an imaging process so as to remain motionless.

Overall this handle assembly 34 has a U-shape which includes a horizontal base portion 34c and two vertical upwardly-extending branches 34a, 34b that are fixed to the arm 22. Each branch plays the role of a vertical handle portion.

Other assemblies may alternatively be used for handling the arm 22.

Patient positioning arm 22 may also support a monitor or display assembly 36 which makes it possible for a practitioner of the apparatus to view images displayed thereon, interact therewith and drive certain functions of the apparatus.

Figure 2:
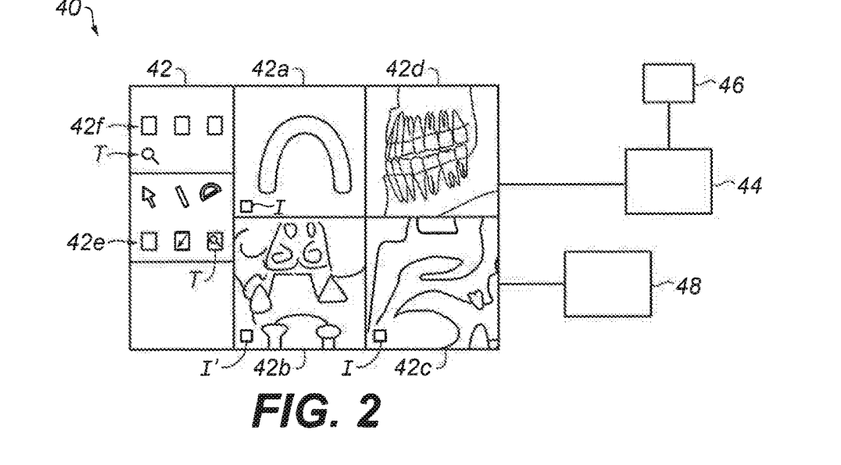
FIG. 2 shows main functional components or assemblies of an interface x-ray CT imaging system according to an embodiment of the invention.

FIG. 2 is a schematic view of main functional components or assemblies that can be used in exemplary method and/or apparatus embodiments herein. System 40 is an x-ray CT imaging interface system and here, more particularly, a CBCT imaging interface system, that may be part of apparatus 10 or not. For example, system 40 may be located in the arm 22 of apparatus 10 or remotely-located relative to the apparatus (e.g. in or coupled to the same room or in a separate room or in another place).

In one exemplary embodiment, system 40 is located in the apparatus but all the following description applies equally if system 40 is distinct from the apparatus.

System 40 comprises a display assembly 42, here a monitor or screen or several of them, that may correspond to display assembly 36 of FIG. 1. Display assembly 42 may display selected images of a patient's maxillofacial region obtained from a CBCT imaging process performed by the apparatus 10. As very schematically illustrated in FIG. 2, four images may be displayed on the same screen at a time: three sectional views 42a-c (axial view 42a, coronal or frontal view 42b and sagittal view 42c) and a 3D view 42d (left right). However, a different number of views may be displayed (ex: 1, 2, 3 or more than 4) or the same views but according to another geometrical arrangement.

System 40 also comprises a control assembly 44 that is connected to display assembly 42. Control assembly 44 includes in particular a processor and possibly one or more storage medium for storing a computer program having instructions for controlling system 40 to practice exemplary method embodiments. When the processor executes the computer program stored in the one or more storage medium the processor is considered as being configured to perform steps or operations of the method according to the present invention.

An aspect of the application is also directed to a computer program product including the one or more storage medium.

The above one or more storage medium may be, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store such a computer program.

Control assembly 44 may be used only for practicing exemplary methods of operating the interface CBCT imaging system 40.

Alternatively or in addition, control assembly 44 may be used to enable operation of the apparatus 10 and its different components/assemblies, in particular to perform a CBCT scan and reconstruct 3D volumes (3D x-ray image data). In that regard, the stored computer program(s) have instructions for controlling the apparatus 10 to practice a method for obtaining a 3D volume.

System 40 also comprises one or more external storage medium 46 that store, here, different volumes of data reconstructed by the apparatus in the course of the CBCT imaging process. The one or more external storage medium 46 may also be of the same type as described above.

The one or more external storage medium 46 may also store the above computer program(s) for controlling system 40 and/or, more generally, for controlling the apparatus 10 instead of the one or more external storage medium of control assembly 44.

System 40 further comprises a user interface assembly that allows a user, e.g. a practitioner or technician, to interact with the display assembly 42, and possibly control assembly 44 that executes image processing/algorithms, in order to perform different tasks.

The user interface assembly may include one or more interaction devices 48 connected to display assembly, such as, but not limited to, a pointing device, e.g. a computer mouse joystick, a stylet, a keypad, a touchpad etc.

Other types of interaction devices or tools (user interface tools) may alternatively, or in addition, be used: a touch screen, tool icons displayed or that may be displayed on command on the screen etc.

FIG. 2 illustrates on the left hand part of the screen 42 several tool icons 42e and 42f displayed next to the displayed images and that can be used by a user to interact with the displayed images for selecting or taking an action. Some of these tool icons may be available to provide functions such as adjustment function (ex: size adjustment).

Tool icons 42e-f can take any of a number of forms known to those skilled in the user interface arts.

An exemplary method embodiment according to the application will now be described with reference to FIG. 3 which depicts an algorithm of the corresponding computer program(s). Here the exemplary method embodiment also includes prior steps that enable obtaining of a 3D volume through the CBCT imaging apparatus 10.

In a first step S1 a CBCT scan of a patient's maxillofacial region is carried out. This scan is obtained by rotating the gantry about the patient's maxillofacial region and acquiring a set of angularly spaced projections (2D images that form a set of data) in the course of the rotational movement thanks to the sensor(s) that receives the cone-shaped beam attenuated by the patient's maxillofacial region.

Second step S2 is a 3D reconstruction volume based on the acquired set of data. Such a reconstruction step is known to the skilled person. Here, preferably two 3D volumes are reconstructed according to two different types of data volumes:

a first 3D volume is a FDK volume (Feldkamp David Kemp) that is obtained through using the FDK algorithm or method (one of the most popular reconstructing methods) applied to all the 2D images (two-stage process including high-frequency filtering and retroprojection);

a second 3D volume is a MAR volume (Metal Artifact Reduction) that is obtained through using a known MAR algorithm or method which helps to reduce metal streak artifacts. In some exemplary embodiments, other or additional (e.g., 3 or more) known reconstructions algorithms can be used for later comparison.

U.S. Pat. No. 6,721,387 describes a method of reducing metal artifacts.

To summarize this exemplary method embodiment comprises several main steps:

reconstructing a preliminary image from input projection data generated by the CBCT imaging system using commonly known filtered back projection;

identifying metal objects in the preliminary image based on the intensity value of the pixels in this image;

generating secondary projections from said input projection data by removing projections of objects having characteristics that may cause the objects to be altered in a final corrected-artifact image;

extracting the projections of metal objects previously identified from the secondary projection data generated at previous step;

generating corrected projections by removing the projections of the metal objects extracted above from said input projection data;

generating a final image by reconstructions said corrected projections generated in previous step and inserting the metal objects identified in the above step into the final image.

Other methods of reducing metal artifacts can alternatively be envisaged such as those described in US 2009074278 and EP 1 846 893.

Then step S2 makes it possible to reconstruct the same maxillofacial region with two different volumes of data (FDK and MAR) which each provide the practitioner with different types of information.

These two different data volumes are stored, e.g. in the storage medium 46 of FIG. 2 (step S3).

Each image or portion of image of the maxillofacial region is therefore available to the practitioner for display either with the FDK data volume or the MAR data volume.

To be noted that steps S1 to S3 may be performed separately from the following steps, e.g., delayed in time and/or executed by distinct entities.

Next step S4 is a displaying step for displaying the three sectional views 42a-c corresponding to a slice in an axial view (42a), a slice in a coronal view (42b) and a slice in sagittal view (42c) respectively. These views are obtained through the 3D reconstructed volume, i.e. either the FDK or MAR volume. A different number of sectional views may alternatively be displayed.

In one exemplary embodiment, for instance the MAR volume is used first for displaying the above sectional views in order to provide the practitioner with high contrast-to-noise ratio views and reduced metal streak artifacts.

Figure 4:
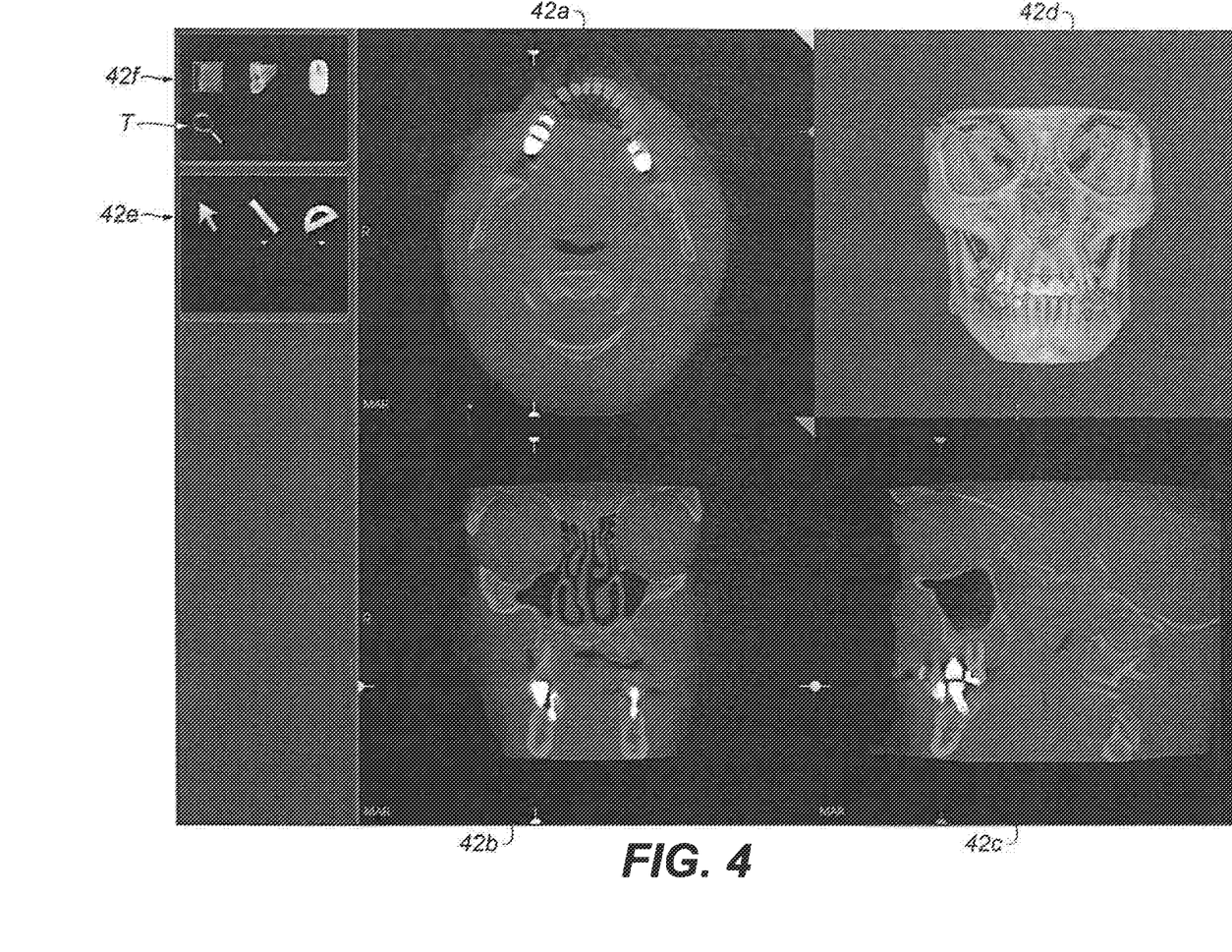
FIGS. 4 to 7 show different sets of sectional views or slices illustrating different steps or aspects of the method of FIG. 3.

FIG. 4 illustrates the above views displayed on the screen with the adjacent tool icons 42e-f.

To be noted that all the displayed views 42a-c are dependent on the same data volume. Initially the displayed views preferably depend on a single reconstruction type.

When the practitioner is interacting with a view on the screen through a user interface tool (ex: the cursor of a mouse) he/she may select another slice within the same view (e.g., axial), e.g. by scrolling with the mouse wheel (e.g., to move through axial slices of the volume). This change in slice leads to corresponding changes at least in one of the other two views where the slice change may have an impact.

In addition a 3D image 42d may also be displayed at the same time on the screen (left right).

Step S5 is a displaying step for displaying a comparison tool or icon T (see FIGS. 2 and 4) which will be used to make a comparison between FDK volume and MAR volume. In FIGS. 2 and 4 this tool T is always visible on the screen in the available tool icons 42f, e.g. under the form of a magnifying glass. In a variant embodiment, this comparison FDK volume/MAR volume tool may be displayed upon command from the user through a user interface tool (keypad, mouse etc.).

An indicator I may also be displayed on each view 42a-c (FIGS. 2 and 4), e.g. at the bottom of each view (step S6). Such an indicator is representative of the type of data volume that is used for displaying the corresponding slice (either FDK or MAR data volume).

In this exemplary embodiment this indicator may be displayed by default by system 40 when the different views are displayed on the screen.

On FIG. 4 the indicator corresponds to the name of the type of data volume displayed, i.e. here MAR. However, other indicators may alternatively be used and positioned at different locations on the screen.

Next step S7 is an activation step for activating/selecting the comparison tool T by the user. This activation step may be performed by using a pointing device such as a computer mouse 48 (FIG. 2) and clicking on the displayed comparison tool T with the cursor of the mouse.

Then the user moves the cursor to a view of his/her choice among the displayed three views 42a-c and selects a region or zone of interest (ROI) on the chosen slice/view (step S8) by appropriately positioning the cursor on the view.

Then the user activates displaying of the ROI (step S9) on the selected slice/view.

Figure 5:
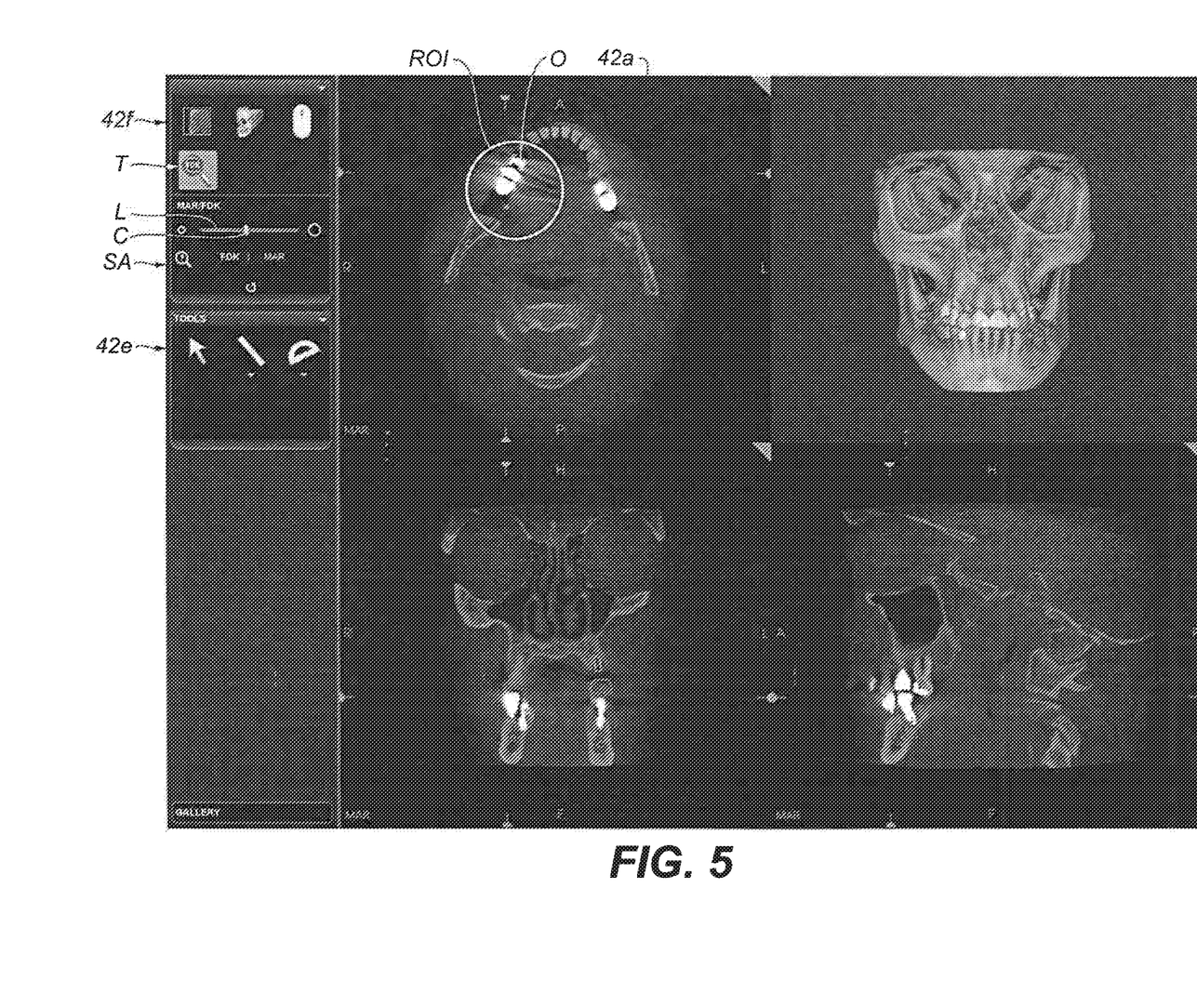

An example of a possible selected ROI is illustrated on the displayed axial slice 42a of FIG. 5 and an outline O of the ROI is displayed. Here the ROI is bounded by an apparent continuous line with a circular shape but other alternative forms may be used (ex: rectangle, square etc.) with a continuous or interrupting line.

An optional step S10 may be performed to adjust the size of the ROI where necessary, e.g. to include more than one tooth in the slice.

When tool icon T has been activated an area SA appears below tool icon T (FIG. 5) and includes a size adjustment cursor C positioned on an horizontal slider L between two extreme circles, a small one and a large one, respectively corresponding to a small size adjustment (reduction in size) and a large size adjustment (increase in size).

Thus size adjustment may be made by moving the mouse cursor to this area SA, positioning it on the cursor C and pressing down the mouse left button to activate size adjustment function. The cursor C is moved left or right depending on the mouse cursor movement while keeping the mouse left button down. Once the appropriate size adjustment has been achieved, the mouse left button is released and the mouse cursor is next moved to the previously area of the selected ROI.

When the mouse left button is pressed down the ROI outline O appears again on the selected location with the desired size.

In a general manner, the setting of the ROI size may be made through any dedicated mechanism such as a slider which will make appear the ROI outline in a given position defined by the computer program(s), e.g., in the middle of an image, so that the user can move the slider and directly see the impact on the ROI size. A default size of the ROI may be defined by the computer program(s).

All that has been described above regarding size adjustment may be performed differently (e.g., through different interface tools) and at another time.

In a variant exemplary embodiment the ROI size may be adjusted directly on the selected view with the selected ROI apparent (the mouse left button is down), e.g. through activating a control key of a keypad (interaction device 48 of FIG. 2) and scrolling the mouse wheel. The size of the ROI therefore changes dynamically on the selected view.

Optionally, a direct ROI size adjustment on the selected view (whatever its implementation and the interface used) may also lead to a corresponding change in the position of the cursor C on the slider L, either at the same time or in a slightly deferred manner. Display of the corresponding position of the cursor C is therefore performed.

The ROI that has been selected by the user, with a possible size adjustment, contains a portion of the data volume of the first type (ex: MAR). This data portion is considered as a first portion of data and appears to be of interest to the user. However, this type of data volume may not be sufficient for the user to make a correct diagnosis.

It is therefore of great interest for the user to view this ROI with another type of data volume which will provide him/her with different/additional information without having to change the whole display of the view.

Figure 3:
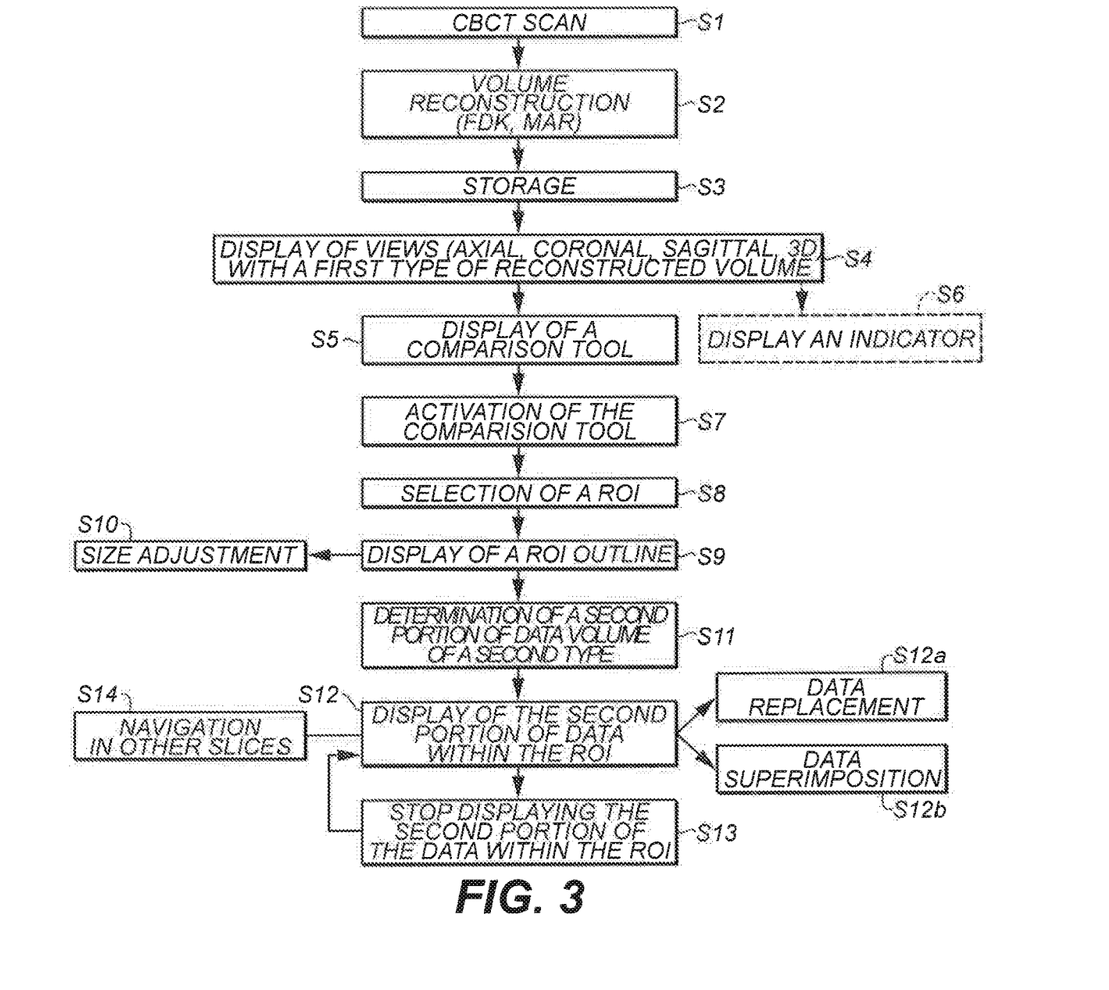
FIG. 3 shows an algorithm of a method according to an embodiment of the invention.

In this respect, at following step S11 of FIG. 3 the first portion of data that corresponds to the selected ROI in the second type of data volume (here the FDK volume) is determined/identified by calculation (by control assembly 44).

Next step S12 makes provision for displaying within the selected ROI (displayed within the apparent outline O) the thus determined second portion of the second type of data volume (FDK localized display) as illustrated in FIG. 5.

In this exemplary embodiment, this displaying step is performed at the same time the outline of the selected ROI is displayed (S9) and therefore is commanded by clicking the mouse left button. Keeping the mouse left button down maintains the display of the second data portion of the second type of data volume.

Thus steps S9, S11 and S12 are performed simultaneously or virtually simultaneously.

However, in a variant exemplary embodiment step S9 may be performed first, including displaying within the outline O the first data portion of the first type. Steps S11 and S12 may then be performed subsequently upon activating another command or interface tool. This provides the advantage of controlling the display of the second type of data.

As briefly mentioned above, size adjustment step S10 may be carried out at another time, for example when the second data portion has been displayed within the outline O. Thus, the display of the second type of data may lead the user to decide for another ROI size.

Size adjustment may also take place at different instant times during the performance of the method.

Of course, all that has been described above with displaying a MAR volume first and next a localized FDK volume applies to the reverse situation: displaying a FDK volume first and next a localized MAR volume, e.g. because the FDK volume includes metallic parts that may affect the visual quality of the image and lead to interpretability errors.

For example, this display may be performed in two ways:
  either the second data portion of the second type of data volume replaces the first data portion of the first type of data volume (step S12a), which requires computational tasks, e.g. from control assembly 44; or
  the second data portion of the second type of data volume is superimposed on the first data portion of the first type of data volume (step S12b), which is the easiest and faster way of proceeding.

Thus, the chosen slice of the patient's maxillofacial region is displayed with the first type of data volume (here MAR volume) except for the ROI that is displayed with the second data portion of the second type of data volume (here the FDK volume). This allows the practitioner to have two types of data within the same view (combined display), providing complimentary information at the same time instead of having to select and display another type of reconstructed data volume for the whole image and shift from one to another several times for comparison purpose.

In one exemplary method embodiment, the superimposed data only is visible. Alternatively, the superimposed data has an adjustable transparency to allow the first type data to be partially visible along with the superimposed data, which has adjustable transparency. In another exemplary method embodiment, only the superimposed data is present the adjustable transparency can be applied to see only the superimposed data.

Certain exemplary method and/or apparatus embodiments can provide a gain of time for the practitioner to make a diagnosis and also simplifies his/her task.

Having on the same slice of the maxillofacial region both a first area displayed with a first type of data volume and a second localized area (ROI) displayed with a second type of data volume also makes it possible to accomplish comparison tasks (dynamically) which were difficult in the prior art. The resulting medical review, analysis or diagnosis may then be of better quality.

To be noted that slices displayed with a MAR reconstructed volume remove artifact. When viewing such slices the user may however be interested locally by the FDK reconstructed volume (more precisely, only by a data portion of the FDK reconstructed volume that corresponds to the selected ROI) to view on the screen anatomical details that might have disappeared with the MAR reconstructed volume.

The user then may dynamically compare between the two reconstructed volumes in order to evaluate the impact of the reconstruction process on the displayed anatomical area.

The exemplary method algorithm of FIG. 3 may further comprise displaying a second indicator representative of the type of data volume that is displayed within the ROI in addition to the first indicator of the type of data volume displayed in the view or views on the screen this second indicator may be located next to the outline of the ROI or at any other place on the view of interest or elsewhere.

In this exemplary embodiment, the inner of the magnifying glass of tool icon T in FIG. 5 indicates "FDK" which corresponds to the second type of data displayed or to be displayed within the selected ROI.

The exemplary method algorithm of FIG. 3 also comprises a further stopping step S13 which allows to stop displaying within the ROI the second portion of the second type of data volume. This therefore causes the first data portion of the first type to be displayed again within the ROI. The user may choose to repeat the steps S12 and S13 several times to locally compare quite easily the different types of data within the same ROI.

Practically, step S12 may be performed very easily by the user by releasing the pressure on the mouse left button. If the mouse click button is pressed again, step S12 is performed again and so on.

This practical implementation makes also very easy for the practitioner to proceed with analysis and/or comparison tasks.

Another step S14 makes provision for navigating inside the reconstructed volume in one selected view and changing the slice of interest by selecting one of possible parallel slices within the same sectional view (ex: axial view).

According to this step, the selected ROI remains displayed within each selected slice (while navigating through the different slices) and the second portion of data of the second type of data volume changes accordingly.

In a practical manner this slice change may be performed by scrolling the mouse wheel when the cursor is on the selected ROI and the click button still pressed.

Figure 6:
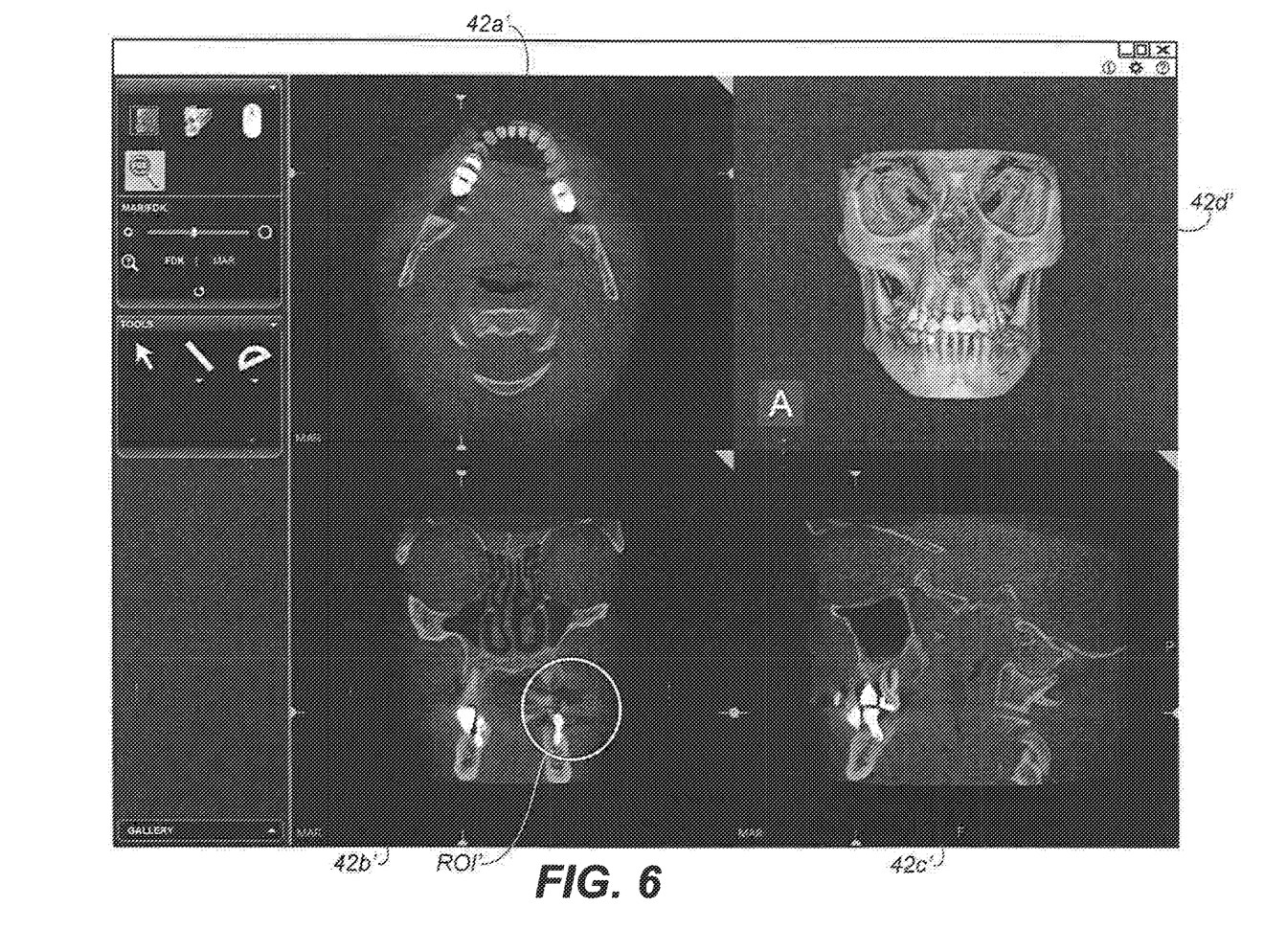

FIG. 6 illustrates another example embodiment according to the invention. Four views 42a', 42b', 42c' and 42d' of a patient's maxillofacial region as in FIGS. 2 and 4 (axial, coronal, sagittal and 3D) are displayed. To be noted that displaying a 3D view is not necessary here as for the other exemplary embodiments and variants.

Here, another ROI' has been selected in the coronal view 42b' and the displayed ROI' contains the second type of data (FDK volume) whereas the whole view is displayed with the first type of data (MAR volume).

Figure 7:
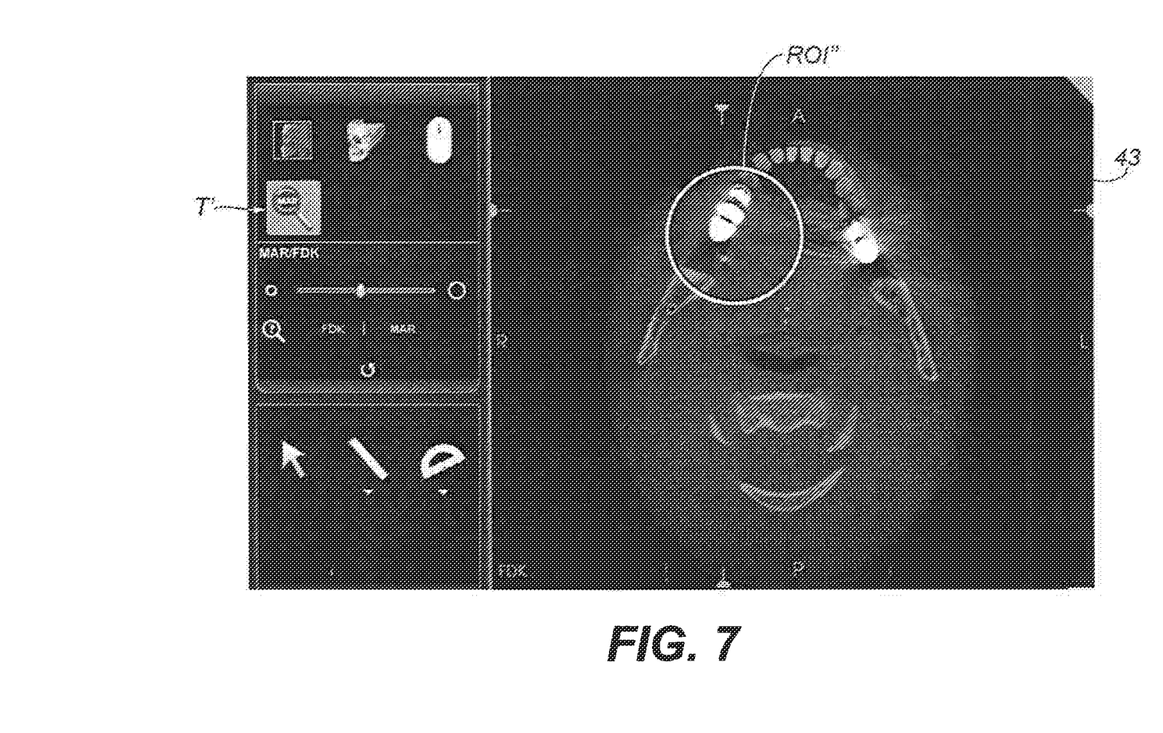

FIG. 7 still illustrates another example embodiment according to the invention in which only an axial view 43 has been displayed. Here, the slice/view is displayed with a first type of data that is FDK volume data whereas a selected ROI" is displayed with a second type of data that is MAR volume data. As indicated, the tool icon T' indicates inside the magnifying glass the second type of data.

All that has been described above still applies to these two example embodiments.

It is to be noted that the functionalities described above may be added in a software product commercialized by the company Carestream Dental under the commercial name "CS 3D imaging software". Exemplary embodiments according to the application can include various features described herein (individually or in combination).

Consistent with exemplary embodiments herein, a computer program can use stored instructions that perform on image data that is accessed from an electronic memory. As can be appreciated by those skilled in the image processing arts, a computer program for operating the imaging system and probe and acquiring image data in exemplary embodiments of the application can be utilized by a suitable, general-purpose computer system operating as CPU 70 as described herein, such as a personal computer or workstation. However, many other types of computer systems can be used to execute the computer program of the present invention, including an arrangement of networked processors, for example. The computer program for performing exemplary method embodiments may be stored in a computer readable storage medium. This medium may include, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. Computer programs for performing exemplary method embodiments may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the application, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the application. Memory is also used as the data workspace for executing and storing intermediate and final results of calculations and other processing. Computer-accessible memory can be volatile, non-volatile, or a hybrid combination of volatile and non-volatile types.

It will be understood that computer program products of the application may make use of various image manipulation algorithms and processes that are well known. It will be further understood that computer program product exemplary embodiments of the application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product exemplary embodiments of the application, are not specifically shown or described herein and may be selected from such algorithms, systems, hardware, components and elements known in the art.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by at least the following claims.

What is claimed is:

1. A method for obtaining a radiographic image of a patient's maxillofacial region through x-ray CT imaging, the method comprising the steps of:
   acquiring a set of data relative to a patient's maxillofacial region through an x-ray CT imaging apparatus;
   reconstructing two types of data volumes from the same acquired set of data including a FDK volume and a MAR (Metal Artifact Reduction) volume that both correspond to the same maxillofacial region;
   displaying at least one slice of the patient's maxillofacial region with a first type of data volume among the FDK volume and the MAR volume;
   selecting a region of interest (ROI) in the displayed at least one slice, the ROI corresponding to a first portion of said first type of data volume; and
   displaying within the selected ROI a second portion of a second type of data volume, the at least one slice of the patient's maxillofacial region being displayed with the first type of data volume while the ROI is displayed with the second portion of the second type of data volume.

2. The method of claim 1, wherein, prior to displaying within the selected ROI the second portion of the second type of data volume, the method comprises a step of determining the second portion of the second type of data volume among the FDK volume and the MAR volume corresponding to the selected ROI.

3. The method of claim 1, wherein the at least one slice of the patient's maxillofacial region comprises a slice in a coronal view, a slice in a facial view and a slice in a sagittal view.

4. The method of claim 3, wherein the ROI is selected among any of the three slices.

5. The method of claim 3, wherein the method further comprises a step of displaying another parallel slice within the same view with the same displayed ROI instead of the previous at least one slice.

6. The method of claim 1, wherein displaying within the selected ROI the second portion of the second type of data volume comprises replacing the first portion of the first type of data volume with the second portion of the second type of volume.

7. The method of claim 1, wherein displaying within the selected ROI the second portion of the second type of data volume comprises superimposing the second portion of the second type of data volume on the first portion of the first type of data volume.

8. The method of claim 1, wherein the method further comprises a step of displaying on the displayed at least one slice an indicator representative of the type of data volume that is used for displaying the at least one slice.

9. The method of claim 1, wherein the method further comprises a step of displaying an indicator representative of the type of data volume that is displayed within the ROI.

10. The method of claim 1, wherein selecting the ROI in the displayed at least one slice comprises beforehand activating a comparison tool FDK volume/MAR volume and moving a pointing device on the displayed at least one slice to a zone of the slice corresponding to the selected ROI.

11. The method of claim 1, wherein the method stops displaying within the selected ROI the second portion of a second type of data volume among the FDK volume and the MAR volume so that the whole at least one slice of the patient's mouth including the ROI is displayed with the first type of data volume.

12. The method of claim 1, wherein the ROI is bounded by an apparent outline.

13. The method of claim 12, wherein the bounding outline has a size that can be adjusted.

14. An x-ray CT imaging interface system, wherein the system comprises:
   a display assembly for displaying a radiographic image of the patient's maxillofacial region;
   a user interface assembly that can be operated by a user for selecting a zone on the displayed image in cooperation with the display assembly;
   a processor configured to:
      display on the display assembly at least one slice of the patient's maxillofacial region with a first type of data volume among a FDK volume and a MAR (Metal Artifact Reduction) volume that respectively correspond to reconstructed data volumes of the same maxillofacial region through x-ray CT imaging;

identify, on the displayed at least one slice, a region of interest (ROI) that has been selected by a user through the user interface assembly and that contains a first portion of the first type of data volume; and display, within the selected ROI, a second portion of a second type of data volume so that the at least one slice of the patient's maxillofacial region is displayed with the first type of data volume while the ROI is displayed with the second portion of the second type of data volume.

15. An x-ray CT imaging apparatus comprising the system of claim 14, wherein the x-ray CT imaging apparatus is configured to:

acquire a set of data relative to the patient's maxillofacial region through an x-ray CT imaging acquisition process; and reconstruct the two types of data volumes from the same acquired set of data that both correspond to the same maxillofacial region.

\* \* \* \* \*